(12) United States Patent
Seo et al.

(10) Patent No.: US 10,165,989 B2
(45) Date of Patent: Jan. 1, 2019

(54) TOMOGRAPHY APPARATUS AND METHOD OF RECONSTRUCTING CROSS-SECTIONAL IMAGE

(71) Applicant: SAMSUNG ELECTRONICS CO., LTD., Suwon-si (KR)

(72) Inventors: Chan-won Seo, Incheon (KR); Toshihiro Rifu, Suwon-si (KR); Duhgoon Lee, Yongin-si (KR); Do-il Kim, Suwon-si (KR); Sang-nam Nam, Suwon-si (KR); Kyoung-yong Lee, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 172 days.

(21) Appl. No.: 15/212,809

(22) Filed: Jul. 18, 2016

(65) Prior Publication Data

US 2017/0069061 A1   Mar. 9, 2017

(30) Foreign Application Priority Data

Sep. 9, 2015   (KR) ........................ 10-2015-0127713

(51) Int. Cl.
*G06K 9/00* (2006.01)
*A61B 6/03* (2006.01)
(Continued)

(52) U.S. Cl.
CPC ............ *A61B 6/032* (2013.01); *A61B 6/5205* (2013.01); *A61B 6/5258* (2013.01); *G06T 11/008* (2013.01); *A61B 6/563* (2013.01)

(58) Field of Classification Search
CPC ............ G06T 11/006; G06T 2211/421; G06T 2207/10081; G06T 2207/20012;
(Continued)

(56) References Cited

U.S. PATENT DOCUMENTS 6,934,357 B2   8/2005   Boyd et al.
7,386,158 B2   6/2008   Yamada
(Continued)

FOREIGN PATENT DOCUMENTS

CN   103198497 A   7/2013
JP   2002-133410 A   5/2002
(Continued)

OTHER PUBLICATIONS

Communication dated Sep. 1, 2016 issued by the Korean Intellectual Property Office in counterpart Korean Patent Application No. 10-2015-0127713.

*Primary Examiner* — Tom Y Lu
(74) *Attorney, Agent, or Firm* — Sughrue Mion, PLLC

(57) ABSTRACT

A tomography apparatus includes a data obtainer configured to obtain first image data at a first point and second image data at a second point using tomography, the tomography being performed by irradiating an X-ray to an object; an image processor configured to perform noise reduction based on at least one from among the first image data and the second image data, and to obtain a first reference image corresponding to the first image data and a second reference image corresponding to the second image data using a result of the performed noise reduction; and an image reconstructor configured to reconstruct a target image representing the object based on the first reference image and the second reference image.

21 Claims, 12 Drawing Sheets

(51) Int. Cl.
*G06T 11/00* (2006.01)
*A61B 6/00* (2006.01)

(58) Field of Classification Search
CPC .......... G06T 2207/30004; G06T 5/002; G06T 5/003; G06T 11/008; A61B 6/032; A61B 6/027; A61B 6/4021; A61B 6/4085; A61B 6/584; A61B 6/00; A61B 6/5205; A61B 6/5258; A61B 6/542
See application file for complete search history.

(56) References Cited

U.S. PATENT DOCUMENTS

| | | |
|---|---|---|
| 7,596,204 B2 | 9/2009 | Ziegler et al. |
| 7,924,972 B2 | 4/2011 | Koehler et al. |
| 8,611,630 B1 * | 12/2013 | Katsevich ............ G06T 7/0012 |
| | | 382/131 |
| 9,060,733 B2 | 6/2015 | Bruder et al. |
| 2013/0308841 A1 | 11/2013 | Yim et al. |
| 2014/0003688 A1 | 1/2014 | Hansis |
| 2014/0029819 A1 | 1/2014 | Zeng et al. |
| 2014/0105477 A1 * | 4/2014 | Ramirez Giraldo ...... G06T 5/50 |
| | | 382/131 |
| 2015/0243056 A1 | 8/2015 | Lee et al. |

FOREIGN PATENT DOCUMENTS

| | | |
|---|---|---|
| JP | 2007-530087 A | 11/2007 |
| JP | 2008-532684 A | 8/2008 |
| JP | 2014-517713 A | 7/2014 |
| KR | 10-2013-0128690 A | 11/2013 |
| KR | 10-2014-0042809 A | 4/2014 |
| KR | 10-2015-0100126 A | 9/2015 |

* cited by examiner

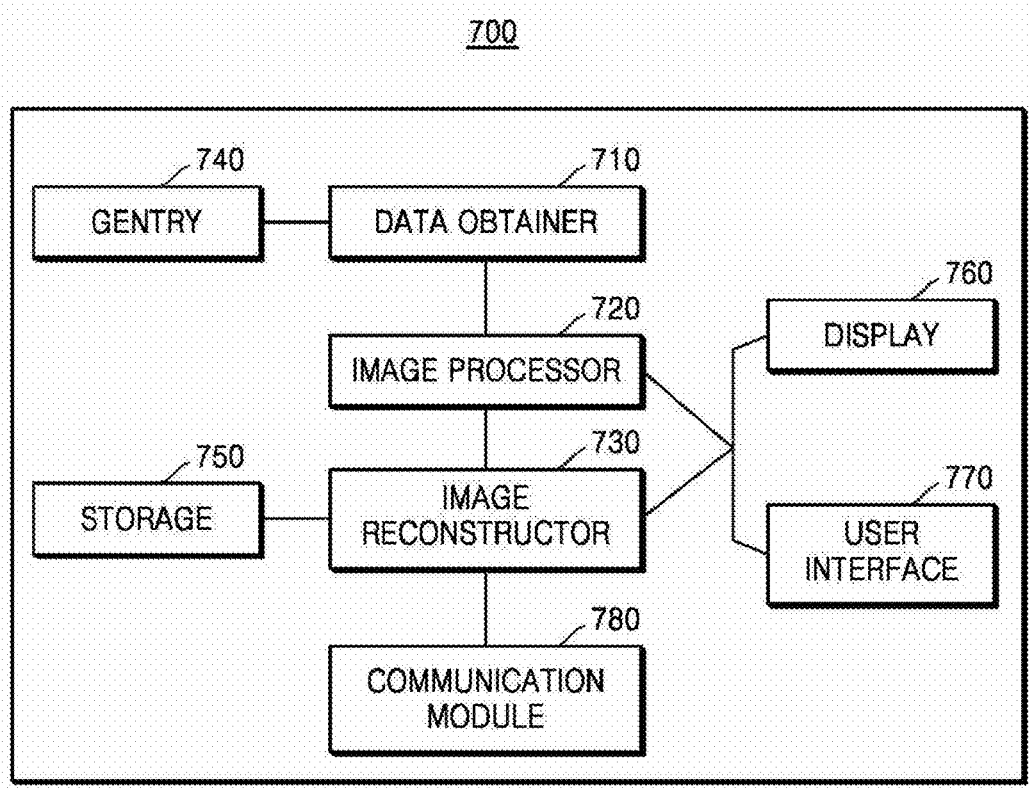

TOMOGRAPHY APPARATUS AND METHOD OF RECONSTRUCTING CROSS-SECTIONAL IMAGE

CROSS-REFERENCE TO RELATED APPLICATION

This application claims priority from Korean Patent Application No. 10-2015-0127713, filed on Sep. 9, 2015, in the Korean Intellectual Property Office, the disclosure of which is incorporated herein in its entirety by reference.

BACKGROUND

1. Field

The present disclosure relates to tomography apparatuses and methods of reconstructing a cross-sectional image.

2. Description of Related Art

A medical imaging apparatus is equipment for obtaining an inner structure of an object in the form of an image. A medical image processor is a noninvasive test apparatus and captures images of structural details inside a body, an internal tissue, flow of fluid, etc., processes the images, and shows the images to a user. A user such as a doctor may diagnose a patient's heath state and disease by using a medical image output from the medical image processor.

As a representative apparatus for capturing an image of an object by irradiating an X-ray to a patient, a computed tomography (CT) apparatus is used.

Since a CT apparatus, which is a tomography apparatus among medical imaging processors, may provide a cross-sectional image of an object, and have an advantage capable of expressing internal structures (for example, organs such as a kidney and a lung) of the object such that the internal structures do not overlap each other compared with a general X-ray apparatus, the CT apparatus is widely used for accurate diagnosis of a disease. Hereinafter, a medical image obtained by the tomography apparatus is referred to as a cross-sectional image.

In obtaining a cross-sectional image, raw data is obtained by performing tomography on an object via a CT apparatus. Also, a cross-sectional image is reconstructed by using the obtained raw data. Here, the raw data may be projection data obtained by projecting an X-ray to an object, or a sinogram which is a set of projection data.

SUMMARY

Provided are tomography apparatuses and methods of reconstructing a cross-sectional image which may reconstruct a noise-free cross-sectional image.

Additional aspects will be set forth in part in the description which follows and, in part, will be apparent from the description, or may be learned by practice of the presented exemplary embodiments.

According to an aspect of an exemplary embodiment, a tomography apparatus includes a data obtainer configured to obtain first image data at a first point and second image data at a second point using tomography, the tomography being performed by irradiating an X-ray to an object; an image processor configured to perform noise reduction based on at least one from among the first image data and the second image data, and to obtain a first reference image corresponding to the first image data and a second reference image corresponding to the second image data using a result of the performed noise reduction; and an image reconstructor configured to reconstruct a target image representing the object based on the first reference image and the second reference image.

The image reconstructor may be further configured to obtain motion information estimating a motion of the object based on the first reference image and the second reference image, and to reconstruct the target image representing the object at a target point based on the motion information.

The first image data and the second image data may be obtained from at least one from among an X-ray based on a first threshold dose, an X-ray based on a first threshold voltage, and an X-ray based on a first threshold current.

The image processor may be further configured to perform the noise reduction based on a dose of the X-ray detected from the at least one from among the first image data and the second image data.

The image processor may be further configured to perform the noise reduction using a low pass filter.

The image processor may be further configured to detect an edge region from at least one of a first image obtained from the first image data and a second image obtained from the second image data, and to perform the noise reduction based on the edge region.

The image processor may be further configured to remove noise while conserving the edge region.

The image processor may be further configured to perform the noise reduction by applying a predetermined model to at least one of the first image data and the second image data.

The predetermined model may include at least one from among a model reflecting geometry information of a tomography apparatus irradiating the X-ray, a model reflecting a characteristic of the X-ray, and a model reflecting a noise characteristic.

The image processor may be further configured to perform the noise reduction by adjusting a size of a voxel inside a first image obtained from the first image data and a size of a voxel inside a second image obtained from the second image data.

The image processor may be further configured to perform the noise reduction by adjusting a thickness of a slice obtained from the first image data and a thickness of a slice obtained from the second image data.

The image processor may be further configured to determine a quality of the first image data and the second image data, and to determine whether to perform the noise reduction depending on the determined quality.

The quality may be determined based on at least one from among a dose of the X-ray and a condition under which the X-ray is irradiated.

The apparatus may further include a display configured to display at least one from among the first reference image, the second reference image, and the target image.

The apparatus may further include a user interface configured to receive a user input using a user interface screen to perform the noise reduction; and a display configured to display the user interface screen.

The apparatus may further include a user interface configured to receive a user input for selecting the first image data and the second image data from among image data corresponding to a plurality of points based on the tomography.

The first reference image may differ from the second reference image in at least one from among a size of the object, a location of the object, and a shape of the object.

According to another aspect of an exemplary embodiment, a method of reconstructing a cross-sectional image includes obtaining first image data at a first point and second image data at a second point using tomography, the tomography being performed by irradiating an X-ray to an object; performing noise reduction based on at least one from among the first image data and the second image data; obtaining a first reference image corresponding to the first image data and a second reference image corresponding to the second image data using a result of the performed noise reduction; and reconstructing a target image representing the object based on the first reference image and the second reference image.

The reconstructing of the target image representing the object may include: obtaining motion information estimating a motion of the object based on the first reference image and the second reference image; and reconstructing the target image representing the object at a target point based on the motion information.

The performing of the noise reduction may include: performing the noise reduction based on a dose of the X-ray detected from the at least one from among the first image data and the second image data.

The performing of the noise reduction may include: detecting an edge region from at least one from among a first image obtained from the first image data and a second image obtained from the second image data, and performing the noise reduction based on the edge region.

The performing of the noise reduction may include at least one from among: adjusting a size of a voxel inside a first image obtained from the first image data and a size of a voxel inside a second image obtained from the second image data, and adjusting a thickness of a slice obtained from the first image data and a thickness of a slice obtained from the second image data.

The performing of the noise reduction may include: determining a quality of the first image data and the second image data, and determining whether to perform the noise reduction depending on the determined quality, and the quality may be determined based on at least one from among a dose of the X-ray and a condition under which the X-ray is irradiated.

The method may further include displaying a user interface screen; and receiving a user input using the user interface screen in order to perform the noise reduction.

According to a further aspect of an exemplary embodiment, a non-transitory computer-readable recording medium having recorded thereon a program for executing a method of reconstructing a cross-sectional image, the method including: obtaining first image data at a first point and second image data at a second point using tomography, the tomography being performed by irradiating an X-ray to an object; performing noise reduction based on at least one from among the first image data and the second image data; obtaining a first reference image corresponding to the first image data and a second reference image corresponding to the second image data using a result of the performed noise reduction; and reconstructing a target image representing the object based on the first reference image and the second reference image.

BRIEF DESCRIPTION OF THE DRAWINGS

These and/or other aspects will become apparent and more readily appreciated from the following description of the exemplary embodiments, taken in conjunction with the accompanying drawings in which:

FIG. 7 is a block diagram illustrating a tomography apparatus according to another exemplary embodiment;

DETAILED DESCRIPTION

Figure 1:
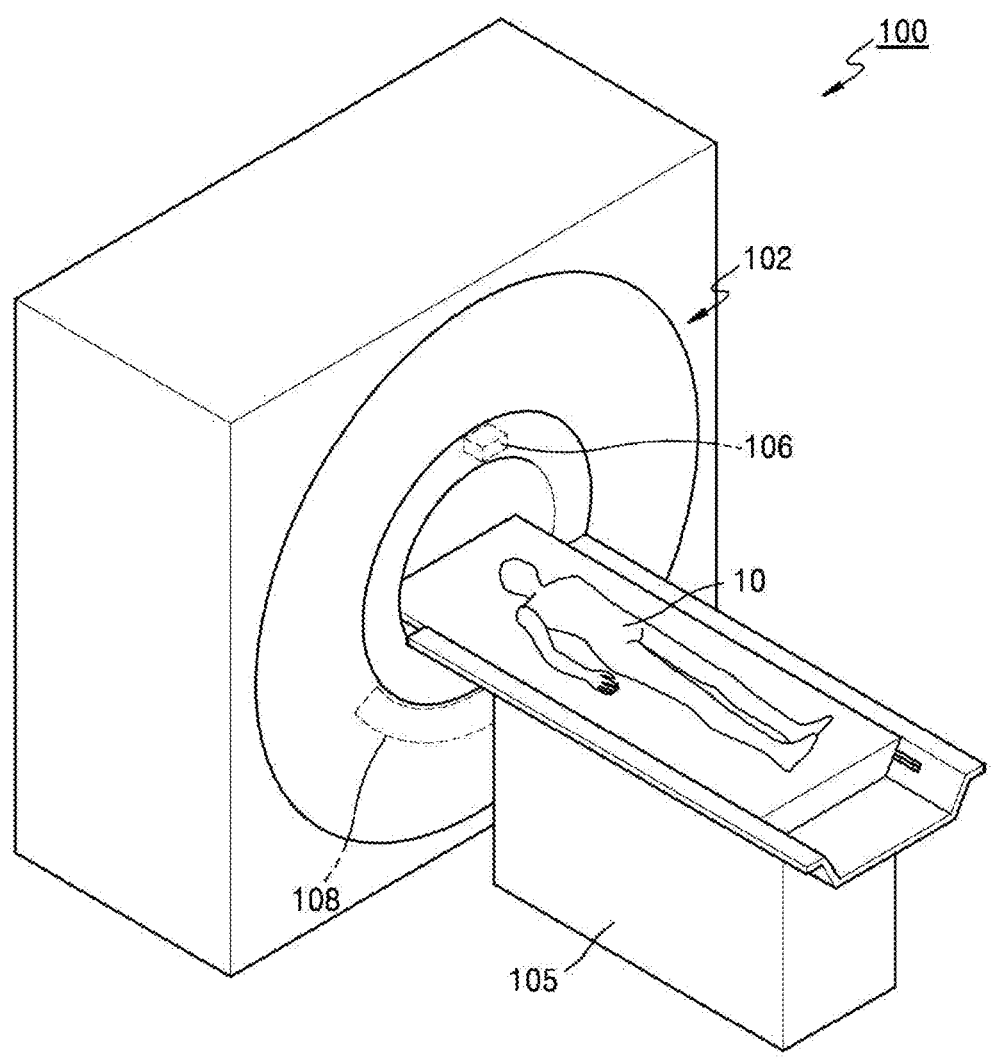
FIG. 1 is a diagram illustrating a general CT system according to an exemplary embodiment.

The attached drawings for illustrating exemplary embodiments of the present disclosure are referred to in order to gain a sufficient understanding of the present disclosure, the merits thereof, and the objectives accomplished by the implementation of the present disclosure. In this regard, the present exemplary embodiments may have different forms and should not be construed as being limited to the descriptions set forth herein. Rather, these exemplary embodiments are provided so that this disclosure will be thorough and complete and will fully convey the concept of the present exemplary embodiments to one of ordinary skill in the art. Like reference numerals refer to like elements throughout the specification.

Hereinafter, the terms used in the specification will be briefly defined, and the exemplary embodiments will be described in detail.

The terms used in this specification are those general terms currently widely used in the art in consideration of functions regarding the present disclosure, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the exemplary embodiments.

When a part "includes" or "comprises" an element, unless there is a particular description contrary thereto, the part can further include other elements, not excluding the other elements. Also, the term "unit" in the exemplary embodiments means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Reference will now be made in detail to exemplary embodiments, examples of which are illustrated in the accompanying drawings. In this regard, the present exemplary embodiments may have different forms and should not be construed as being limited to the descriptions set forth herein. In the following description, well-known functions or constructions are not described in detail so as not to obscure the exemplary embodiments with unnecessary detail.

Throughout the specification, an "image" may mean multi-dimensional data formed of discrete image elements, e.g., pixels in a two-dimensional (2D) image and voxels in a three-dimensional (3D) image. For example, the image may include a medical image of an object which is captured by a computed tomography (CT) imaging apparatus.

In the present specification, a "cross-sectional image" is an image obtained when a tomography apparatus performs tomography on an object, and may denote an image imaged by using projected data after irradiating a beam such as an X-ray to an object. Throughout the specification, a "CT image" may mean an image generated by synthesizing a plurality of X-ray images that are obtained by photographing an object while a CT imaging apparatus rotates around at least one axis with respect to the object.

Furthermore, in the present specification, an "object" may be a human, an animal, or a part of a human or animal. For example, the object may be an organ (e.g., the liver, heart, womb, brain, breast, or abdomen), a blood vessel, or a combination thereof. The object may be a phantom. The phantom means a material having a density, an effective atomic number, and a volume that are approximately the same as those of an organism. For example, the phantom may be a spherical phantom having properties similar to the human body.

Throughout the specification, a "user" may be, but is not limited to, a medical expert including a medical doctor, a nurse, a medical laboratory technologist, a medial image expert, or a technician who repairs a medical apparatus.

Since a CT system is capable of providing a cross-sectional image of an object, the CT system may distinctively express an inner structure, e.g., an organ such as a kidney or a lung, of the object, compared to a general X-ray imaging apparatus.

Specifically, a tomography system 100 may include all tomography apparatuses such as a CT apparatus, an optical coherence tomography (OCT) apparatus, or a positron emission tomography (PET)-CT apparatus.

Hereinafter, for the tomography system 100, a CT system is described as an example.

The CT system may obtain a plurality of pieces of image data with a thickness not more than 2 mm several tens to several hundred times per second and then may process the plurality of pieces of image data, so that the CT system may provide a relatively accurate cross-sectional image of the object. According to the related art, only a horizontal cross-sectional image of the object can be obtained, but this issue has been overcome due to various image reconstruction methods. Examples of 3D image reconstruction methods are as below:

Shade surface display (SSD)—an initial 3D imaging method of displaying only voxels having a predetermined Hounsfield Units (HU) value.

Maximum intensity projection (MIP)/minimum intensity projection (MinIP)—a 3D imaging method of displaying only voxels having the greatest or smallest HU value from among voxels that construct an image.

Volume rendering (VR)—an imaging method capable of adjusting a color and transmittance of voxels that constitute an image, according to areas of interest.

Virtual endoscopy—a method that allows endoscopy observation in a 3D image that is reconstructed by using the VR method or the SSD method.

Multi-planar reformation (MPR)—a method of reconstructing an image into a different cross-sectional image. A user may reconstruct an image in any desired direction.

Editing—a method of editing adjacent voxels so as to allow a user to easily observe an area of interest in volume rendering.

Voxel of interest (VOI)—a method of displaying only a selected area in volume rendering.

A CT system 100 according to an exemplary embodiment will now be described with reference to FIG. 3. The CT system 100 may include various types of devices.

FIG. 1 schematically illustrates the CT system 100. Referring to FIG. 3, the CT system 100 may include a gantry 102, a table 105, an X-ray generator 106, and an X-ray detector 108.

The gantry 102 may include the X-ray generator 106 and the X-ray detector 108.

An object 10 may be positioned on the table 105.

The table 105 may move in a predetermined direction (e.g., at least one of up, down, right, and left directions) during a CT imaging procedure. Also, the table 105 may tilt or rotate by a predetermined angle in a predetermined direction.

The gantry 102 may also tilt by a predetermined angle in a predetermined direction.

Figure 2:
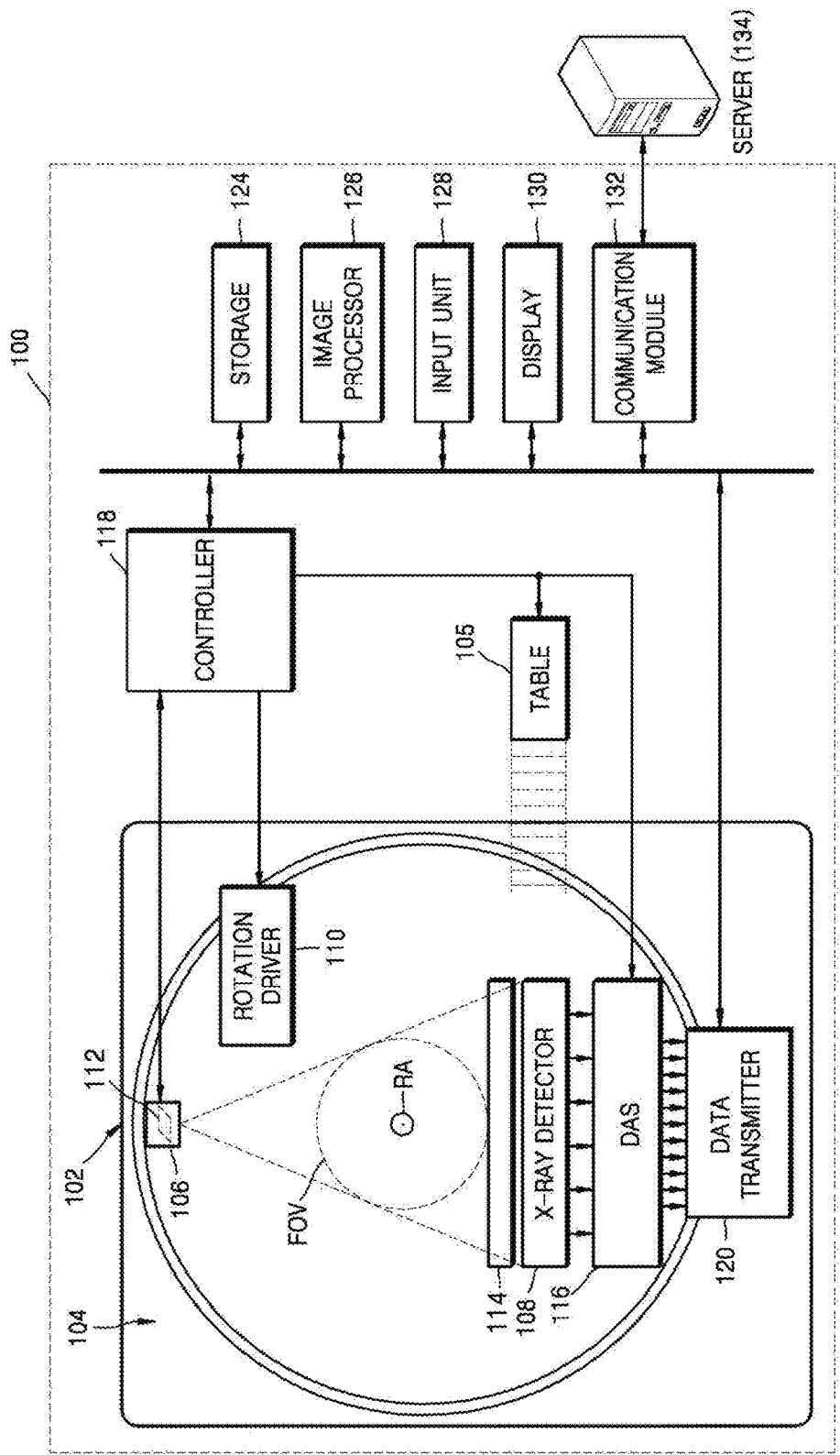
FIG. 2 is a diagram illustrating a configuration of a CT system according to an exemplary embodiment.

FIG. 2 is a block diagram illustrating a structure of the CT system 100.

The CT system 100 may include the gantry 102, the table 105, a controller 118, a storage 124, an image processor 126, an input unit 128, a display 130, and a communication module 132.

As described above, the object 10 may be positioned on the table 105. In the present exemplary embodiment, the table 105 may move in a predetermined direction (e.g., at least one of up, down, right, and left directions), and movement of the table 105 may be controlled by the controller 118.

The gantry 102 may include a rotating frame 104, the X-ray generator 106, the X-ray detector 108, a rotation driver 110, a data acquisition system (DAS) 116, and a data transmitter 120.

The gantry 102 may include the rotating frame 104 having a loop shape capable of rotating with respect to a predetermined rotation axis RA. Also, the rotating frame 104 may have a disc shape.

Figure 4A:
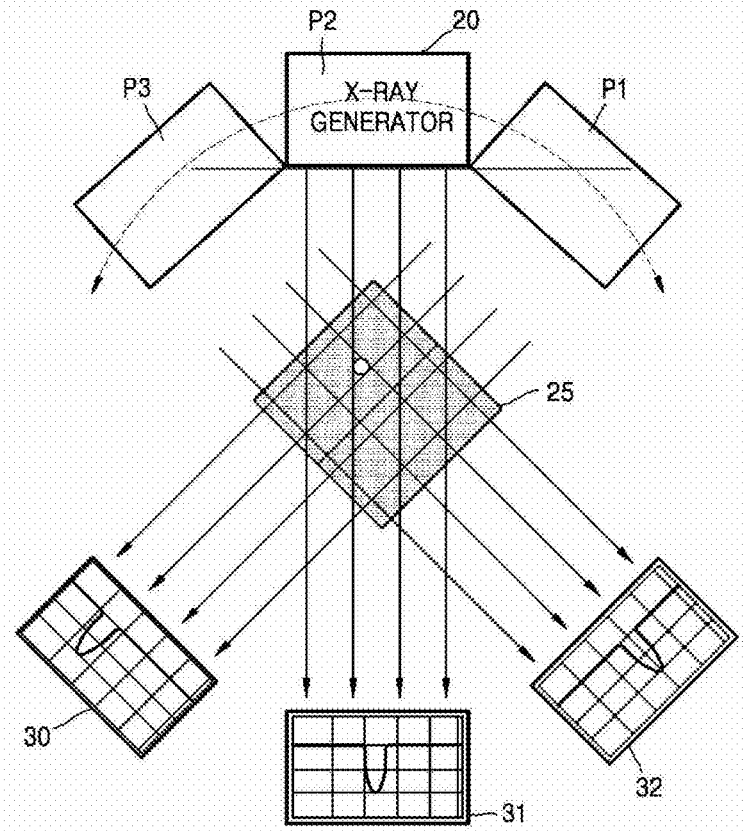
FIG. 4A and FIG. 4B are diagrams for explaining CT image capturing and reconstructing operations according to an exemplary embodiment.
Figure 4B:
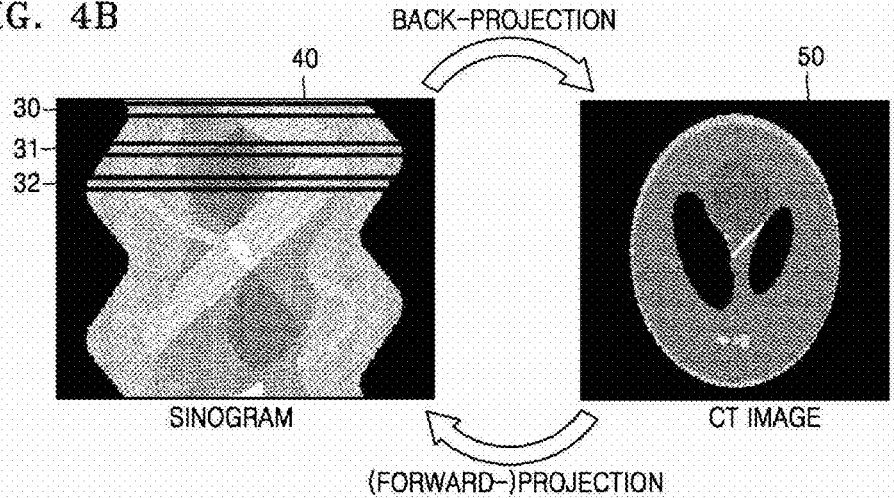

The rotating frame 104 may include the X-ray generator 106 and the X-ray detector 108 that are arranged to face each other so as to have predetermined fields of view FOV. The rotating frame 104 may also include an anti-scatter grid 114. The anti-scatter grid 114 may be positioned between the X-ray generator 106 and the X-ray detector 108. Though FIG. 4A and FIG. 4B illustrate a case where the rotating frame 104 includes one X-ray generator 106 as an example, the rotating frame 104 may include a plurality of X-ray generators. Also, in the case where the rotating frame 104 includes the plurality of X-ray generators, the rotating frame 104 includes a plurality of X-ray detectors corresponding to the plurality of X-ray generators. Specifically, one X-ray generator 106 becomes one X-ray source. For example, in the case where the rotating frame 104 includes two X-ray generators 106, the rotating frame 104 is referred to as including a dual source. Hereinafter, in the case where the rotating frame 104 includes one X-ray generator 106, the one X-ray generator 106 included in the rotating frame 104 is referred to as a 'single source', and in the case where the rotating frame 104 includes two X-ray generators (not shown), the two X-ray generators (not shown) included in the rotating frame 104 are referred to as a 'dual source'. Also, in the two X-ray generators forming the dual source, one X-ray generator is referred to as a 'first source', and the other X-ray generator is referred to as a 'second source'. Also, a tomography system 100 in the case where the rotating frame 104 includes one X-ray generator 106 is referred to as a 'single source tomography apparatus', and a tomography system 100 in the case where the rotating frame 104 includes two X-ray generators is referred to as a 'dual source tomography apparatus'. In a medical imaging system, X-ray radiation that reaches a detector (or a photosensitive film) includes not only attenuated primary radiation that forms a valuable image but also scattered radiation that deteriorates the quality of an image. In order to transmit most of the primary radiation and to attenuate the scattered radiation, the anti-scatter grid 114 may be positioned between a patient and the detector (or the photosensitive film).

For example, the anti-scatter grid 114 may be formed by alternately stacking lead foil strips and an interspace material such as a solid polymer material, solid polymer, or a fiber composite material. However, formation of the anti-scatter grid 114 is not limited thereto.

The rotating frame 104 may receive a driving signal from the rotation driver 110 and may rotate the X-ray generator 106 and the X-ray detector 108 at a predetermined rotation speed. The rotating frame 104 may receive the driving signal and power from the rotation driver 110 while the rotating frame 104 contacts the rotation driver 110 via a slip ring (not shown). Also, the rotating frame 104 may receive the driving signal and power from the rotation driver 110 via wireless communication.

The X-ray generator 106 may receive a voltage and current from a power distribution unit (PDU) (not shown) via a slip ring (not shown) and then a high voltage generator (not shown), and may generate and emit an X-ray. When the high voltage generator applies predetermined voltage (hereinafter, referred to as a tube voltage) to the X-ray generator 106, the X-ray generator 106 may generate X-rays having a plurality of energy spectra that correspond to the tube voltage.

The X-ray generated by the X-ray generator 106 may be emitted in a predetermined form due to a collimator 112.

The X-ray detector 108 may be positioned to face the X-ray generator 106. The X-ray detector 108 may be positioned to face the X-ray generator 106. Each of the plurality of X-ray detecting devices may establish one channel but one or more exemplary embodiments are not limited thereto.

The X-ray detector 108 may detect the X-ray that is generated by the X-ray generator 106 and that is transmitted through the object 10, and may generate an electrical signal corresponding to intensity of the detected X-ray.

The X-ray detector 108 may include an indirect-type X-ray detector for detecting radiation after converting the radiation into light, and a direct-type X-ray detector for detecting radiation after directly converting the radiation into electric charges. The indirect-type X-ray detector may use a scintillator. Also, the direct-type X-ray detector may use a photon counting detector. The DAS 116 may be connected to the X-ray detector 108. Electrical signals generated by the X-ray detector 108 may be acquired by the DAS 116. Electrical signals generated by the X-ray detector 108 may be acquired by wire or wirelessly by the DAS 116. Also, the electrical signals generated by the X-ray detector 108 may be provided to an analog-to-digital converter (not shown) via an amplifier (not shown).

According to a slice thickness or the number of slices, only some of a plurality of pieces of data collected by the X-ray detector 108 may be provided to the image processor 126 via the data transmitter 120, or the image processor 126 may select only some of the plurality of pieces of data.

Such a digital signal may be provided to the image processor 126 via the data transmitter 120. The digital signal may be provided to the image processor 126 by wire or wirelessly.

The controller 118 may control an operation of each of the elements in the CT system 100. For example, the controller 118 may control operations of the table 105, the rotation driver 110, the collimator 112, the DAS 116, the storage 124, the image processor 126, the input unit 128, the display 130, the communication module 132, or the like.

The image processor 126 may receive data acquired by the DAS 116 (e.g., pure data that is data before processing), via the data transmitter 120, and may perform pre-processing.

The pre-processing may include, for example, a process of correcting a sensitivity irregularity between channels and a process of correcting signal loss due to a rapid decrease in signal strength or due to the presence of an X-ray absorbing material such as metal.

Data output from the image processor 126 may be referred to as raw data or projection data. The projection data may be stored in the storage 124 with imaging conditions (e.g., the tube voltage, an imaging angle, etc.) during the acquisition of data.

The projection data may be a group of data values that correspond to the intensity of the X-ray that has passed through the object 10. For convenience of description, a group of a plurality of pieces of projection data that are simultaneously obtained from all channels at the same imaging angle is referred to as a projection data set.

The storage 124 may include at least one storage medium from among a flash memory-type storage medium, a hard disk-type storage medium, a multimedia card micro-type storage medium, card-type memories (e.g., an SD card, an XD memory, and the like), random access memory (RAM), static random access memory (SRAM), read-only memory (ROM), electrically erasable programmable ROM (EEPROM), programmable ROM (PROM), magnetic memory, a magnetic disc, and an optical disc.

The image processor 126 may reconstruct a cross-sectional image of the object 10 by using the acquired projection data set. The cross-sectional image may be a 3D image. In other words, the image processor 126 may reconstruct a 3D image of the object 10 by using a cone beam reconstruction method or the like, based on the acquired projection data set.

The input unit 128 may receive an external input with respect to an X-ray tomography imaging condition, an image processing condition, or the like. For example, the X-ray tomography imaging condition may include tube voltages, an energy value setting with respect to a plurality of X-rays, a selection of an imaging protocol, a selection of an image reconstruction method, a setting of a FOV area, the number of slices, a slice thickness, a parameter setting with respect to image post-processing, or the like. Also, the image processing condition may include a resolution of an image, an attenuation coefficient setting for the image, setting for an image combining ratio, or the like.

The input unit 128 may include a device for receiving a predetermined input from an external source For example, the input unit 128 may include a microphone, a keyboard, a mouse, a joystick, a touch pad, a touch pen, a voice recognition device, a gesture recognition device, or the like.

The display 130 may display an X-ray image reconstructed by the image processor 126.

Exchanges of data, power, or the like between the aforementioned elements may be performed by using at least one of wired communication, wireless communication, and optical communication.

The communication module 132 may perform communication with an external device, an external medical apparatus, etc. via a server 134 or the like. The communication will now be described with reference to FIG. 3.

Figure 3:
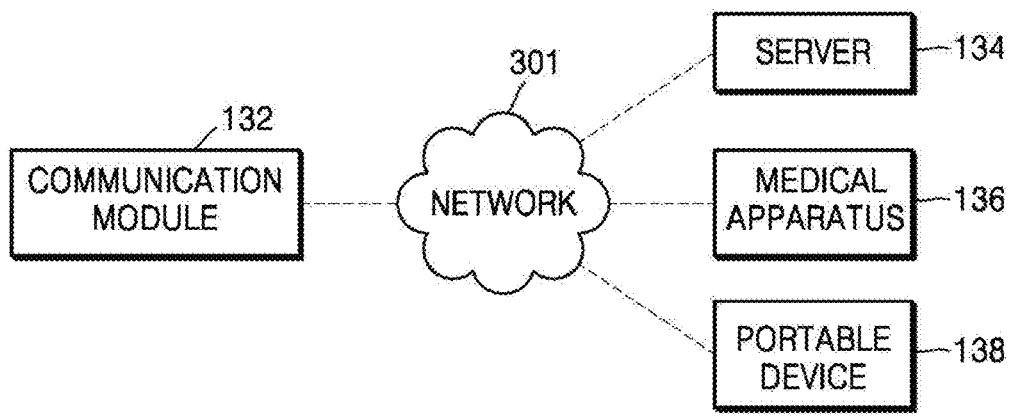
FIG. 3 is a block diagram illustrating a configuration of a communication module of FIG. 1 according to an exemplary embodiment.

FIG. 3 is a block diagram illustrating the communication performed by the communication module 132.

The communication module 132 may be connected with a network 301 and may perform communication with an external device such as the server 134, an external medical apparatus 136, or a portable device 138. The communication module 132 may exchange data with a hospital server or other medical apparatuses in a hospital connected via a picture archiving and communication system (PACS).

Also, the communication module 132 may perform data communication with the external apparatus 138 or the like, according to the digital imaging and communications in medicine (DICOM) standard.

The communication module 132 may transmit and receive data related to diagnosing the object 10, via the network 301. Also, the communication module 132 may transmit and receive a medical image obtained from the medical apparatus 136 such as a magnetic resonance imaging (MRI) apparatus, an X-ray apparatus, or the like.

Furthermore, the communication module 132 may receive a diagnosis history or a medical treatment schedule about a patient from the server 134 and may use the diagnosis history or the medical treatment schedule to diagnose the patient. Also, the communication module 132 may perform data communication not only with the server 134 or the medical apparatus 136 in a hospital but also with the portable device 138 of a user or patient.

Also, the communication module 132 may transmit information about a device error, information about a quality control status, or the like to a system manager or a service manager via the network 301, and may receive a feedback regarding the information from the system manager or service manager.

FIG. 4A and FIG. 4B are a diagram for explaining CT image capturing and reconstructing operations according to an exemplary embodiment.

Specifically, FIG. 4A is a diagram for explaining a CT image capturing operation of a CT apparatus performing CT capturing while rotating around an object 25, and obtaining raw data corresponding to the CT capturing. Also, FIG. 4B is a diagram for explaining a sinogram and a reconstructed CT image obtained by CT capturing.

The CT apparatus generates an X-ray and irradiates the X-ray to an object, and an X-ray detector (not shown) detects an X-ray that has passed through the object. Also, the X-ray detector (not shown) generates raw data corresponding to the detected X-ray.

Specifically, referring to FIG. 4A, an X-ray generator 20 included in a CT apparatus irradiates an X-ray to the object 25. While the CT apparatus performs CT capturing, the X-ray generator 20 rotates around the object and obtains a plurality of raw data 30, 31, and 32 corresponding to rotated angles. Specifically, the CT apparatus obtains first raw data 30 by detecting an X-ray applied to the object at a location P1, obtains second raw data 31 by detecting an X-ray applied to the object at a location P2, and obtains third raw data 32 by detecting an X-ray applied to the object at a location P3. Here, the raw data may be projection data.

To generate one cross-sectional CT image, the X-ray generator 20 should perform CT capturing while rotating 180 degrees at least.

Referring to FIG. 4B, as described in FIG. 4A, one sinogram 40 may be obtained by combining the plurality of projection data 30, 31, and 32 obtained while the X-ray generator 20 moves every predetermined angle interval. The sinogram 40 is a sinogram obtained by CT capturing while the X-ray generator 20 rotates by one period. The sinogram 40 corresponding to rotation of one period may be used for generating one cross-sectional CT image. Rotation of one period may be about a half rotation or more, or one rotation or more depending on specification of the CT system.

Also, a CT image 50 is reconstructed by performing filtered back-projection after the sinogram 40 is filtered.

Figure 5:
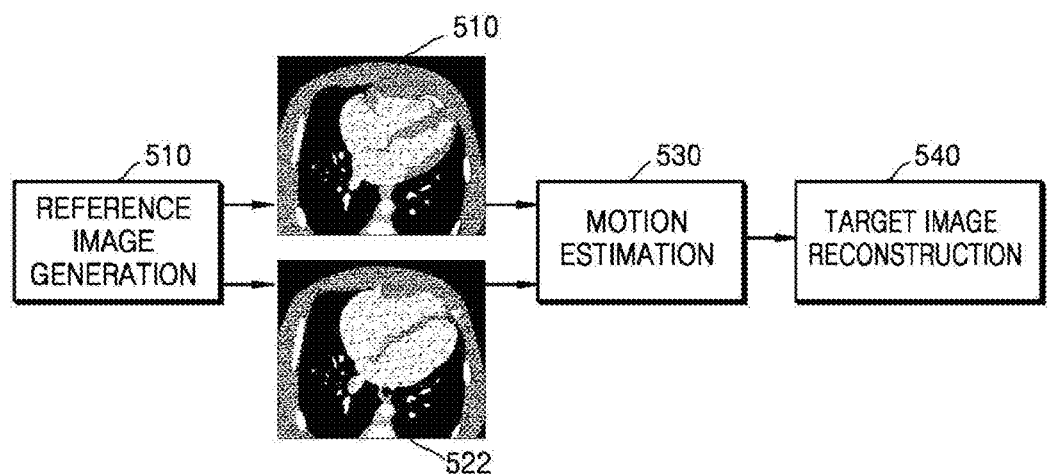
FIG. 5 is a block diagram for explaining an operation of a tomography apparatus according to an exemplary embodiment.

FIG. 5 is a block diagram for explaining an operation of a tomography apparatus according to an exemplary embodiment.

The tomography apparatus may operate to perform tomography by irradiating an X-ray to an object. The tomography apparatus may generate a reference image via tomography (510). The reference image may be used for reconstructing a target image of the object at a target point. The tomography apparatus may use two reference images 521 and 522 in order to reconstruct the target image. Also, the tomography apparatus may reconstruct the target image at the target point by using at least two reference images.

The tomography apparatus may obtain motion information estimating motion of an object based on the first reference image 521 and the second reference image 522 (530). The tomography apparatus may reconstruct a target image representing an object at a target point based on the motion information (540). Here, various reconstruction methods may be used for reconstructing a cross-sectional image. For example, as a method of reconstructing a cross-sectional image at the tomography apparatus, filtered back-projection, an iterative method, etc. may be used.

Figure 6:
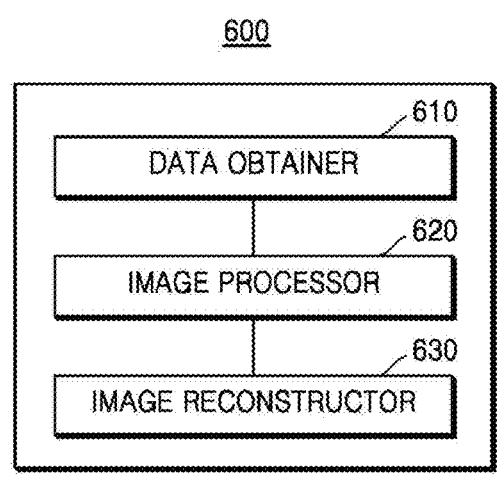
FIG. 6 is a block diagram illustrating a tomography apparatus according to an exemplary embodiment.

FIG. 6 is a block diagram illustrating a tomography apparatus 600 according to an exemplary embodiment.

The tomography apparatus 600 may be included inside the CT system 100 described in FIGS. 1 and 2. Also, the tomography apparatus 600 may be included inside the medical apparatus 136 or the portable device 138 described in FIG. 3, and connected with the CT system 100 to operate. Specifically, the tomography apparatus 600 may be all medical imaging apparatuses reconstructing an image based on data obtained by using a ray that has passed through an object. That is, the tomography apparatus 600 may be all medical imaging apparatuses reconstructing an image based on projection data obtained by using a ray that has passed through the object.

Specifically, the tomography apparatus may be a CT apparatus, an OCT apparatus, or a PET-CT apparatus, etc. Therefore, a cross-sectional image obtained by the tomography apparatus may be a CT image, an OCT image, a PET image, etc. In the following, the accompanying drawings illustrate a CT image as an example of a cross-sectional image. Also, the tomography apparatus 600 may be an MRI apparatus. Also, in the case where the tomography apparatus 600 is included in the tomography system 100 described in FIG. 1, a data obtainer 610, an image processor 620, and an image reconstructor 630 illustrated in FIG. 6 may be included in the image processor 126 of FIG. 2.

According to an exemplary embodiment, the tomography apparatus 600 may include the data obtainer 610, the image processor 620, and the image reconstructor 630. However, all of the illustrated components are not essential components. The tomography apparatus 600 may include a number of components greater than a number of the illustrated components, or include a number of components less than a number of the illustrated components. The components are described below.

The data obtainer 610 may perform tomography on an object and obtain image data corresponding to a point. Specifically, the object may include a predetermined organ. Specifically, the object may include at least one of a heart, an abdomen, a womb, a brain, a breast, and a liver. For example, the object may include a heart expressed by a surface. Here, the heart may include at least one tissue having different brightness values inside a predetermined region.

The data obtainer 610 may obtain first image data at a first point and second image data at a second point. Here, the image data may be raw data obtained by performing tomography. Specifically, the data obtainer 610 may obtain raw data by performing tomography while making less than one rotation. Also, the raw data may be projection data obtained by irradiating radiation to an object, or a sinogram which is a set of projection data. Also, the raw data may be an image generated by performing filtered back-projection on a sinogram.

Specifically, when the X-ray generator 106 at a predetermined location emits an X-ray to an object, a point or a direction in which the X-ray generator 106 views the object is referred to as a view. Projection data denotes raw data obtained in response to one view, and a sinogram denotes raw data obtained by sequentially listing a plurality of projection data.

The data obtainer 610 may obtain the first image data at the first point and the second image data at the second point with respect to the object. The first image data and the second image data may be data obtained by irradiating at least one of an X-ray based on a first threshold dose, an X-ray based on a first threshold voltage, and an X-ray based on a first threshold current to the object.

The image processor 620 may perform noise reduction based on at least one of the first image data and the second image data. The image processor 620 may obtain a first reference image corresponding to the first image data and a second reference image corresponding to the second image data. The image processor 620 may allow the image reconstructor 630 to reconstruct a more accurate target image by reducing noise of the first image data and/or the second image data.

The image processor 620 may perform noise reduction on at least one image data based on an X-ray dose detected from the at least one of the first image data and the second image data. The image processor 620 may perform the noise reduction on at least one image data by using a low pass filter.

The image processor 620 may detect an edge region from at least one of a first image obtained from the first image data and a second image obtained from the second image data, and perform the noise reduction on the at least one image while conserving the edge region.

Also, the image processor 620 may perform noise reduction by applying a model set in advance, or a predetermined model, to the at least one of the first image data and the second image data. Here, the model set in advance may be at least one of a model reflecting geometry information of the tomography apparatus 600 irradiating the X-ray, a model reflecting a characteristic of the X-ray, and a model reflecting a noise characteristic.

The image processor 620 may perform the noise reduction by adjusting a size of a voxel inside the first image obtained from the first image data and a size of a voxel inside the second image obtained from the second image data. For example, the image processor 620 may reduce noise by increasing a size of a voxel.

The image processor 620 may perform the noise reduction by adjusting a thickness of a slice obtained from the first image data and a thickness of a slice obtained from the second image data. For example, the image processor 620 may reduce noise by increasing a thickness of a slice.

The image processor 620 may determine quality of each of the first image data and the second image data, and determine whether to perform the noise reduction depending on the determined quality. That is, the image processor 620 may not perform the noise reduction when quality meets a criterion set in advance, and may perform the noise reduction when quality does not meet the criterion set in advance. The quality may be determined based on at least one of a dose of the X-ray and a condition under which the X-ray is irradiated. For example, the criterion determining the quality may be determined by a number of electrons measured within a scan range, a number of electrons within a scan range after offset correction, a number of electrons detected by an X-ray apparatus, a standard deviation of a number of measured electrons, and a condition under which an X-ray is irradiated (for example, a voltage and a current under which an X-ray is irradiated).

The image reconstructor 630 may reconstruct the target image representing the object based on the first reference image and the second reference image. The image reconstructor 630 may obtain motion information estimating motion of the object based on the first reference image and the second reference image. Here, the image reconstructor 630 may reconstruct the target image representing the object at a target point based on the motion information.

Specifically, the data obtainer 610 obtains first image data from a first angle section corresponding to a first point, and the image processor 620 removes noise of the first image data and obtains a first reference image. Also, the data obtainer 610 obtains second image data from a second angle section corresponding to a second point, and the image processor 620 removes noise of the second image data and obtains a second reference image. Here, the "first angle section" and the "second angle section" denote partial angle sections included in one period angle section less than one rotation. Specifically, the first angle section and the second angle section may have a value less than 180 degrees. Also, the first image and the second image become partial images.

The image reconstructor 630 obtains motion information of an object by using the first reference image and the second reference image. Specifically, the image reconstructor 630 may obtain the motion information representing an amount of motion of the object during a section ranging from the first point to the second point. Here, the motion information may be a difference in at least one of a shape, a size, and a location between a predetermined object included in the first reference image and a predetermined object included in the second reference image occurring due to the motion of the object.

The image reconstructor 630 may reconstruct the target image representing the object at the target point. Here, the target point may be self-set by the image reconstructor 630, or may be set to a predetermined value received from a user. Also, the target point may be a point between the first point and the second point.

FIG. 7 is a block diagram illustrating a tomography apparatus 700 according to another exemplary embodiment.

In FIG. 7, since a data obtainer 710, an image processor 720, and an image reconstructor 730 equally correspond to the data obtainer 610, the image processor 620, and the image reconstructor 630 of FIG. 6, descriptions repeated in FIG. 6 are omitted.

Referring to FIG. 7, the tomography apparatus 700 includes the data obtainer 710, the image processor 720, and the image reconstructor 730. Also, the tomography apparatus 700 may further include at least one of a gentry 740, a storage 750, a display 760, a user interface 770, and a communication module 780. Since the gentry 740, the storage 750, the display 760, the user interface 770, and the communication module 780 included in the tomography apparatus 700 are the same as the gentry 102, the display 130, the input unit 128, the storage 124, and the communication module 132 of the CT system 100 illustrated in FIG. 2 in their operation and configuration, descriptions repeated in FIG. 2 are omitted.

A person of ordinary skill in the art will understand that other general purpose components besides the components illustrated in FIG. 7 may be further included in the tomography apparatus 700.

The data obtainer 710 may obtain image data of an object corresponding to a point by performing tomography on the object. Also, the data obtainer 710 may obtain image data of the object corresponding to a point from an external apparatus.

The gentry 740 includes the X-ray generator 106 (see FIG. 2), the X-ray detector 108 (see FIG. 2), and the DAS 116 (see FIG. 2). The gentry 740 irradiates an X-ray to an object, detects an X-ray that has passed through the object, and generates raw data corresponding to the detected X-ray.

Specifically, the X-ray generator 106 generates an X-ray. Also, the X-ray generator 106 irradiates an X-ray to an object while rotating around the object. Then, the X-ray detector 108 detects an X-ray that has passed through the object. Also, the DAS 116 generates raw data corresponding to the detected X-ray.

The storage 750 may store image data obtained according to tomography. Specifically, the storage 750 may store at least one of projection data and a sinogram which are raw data. Also, the storage 750 may store various kinds of data, a program, etc. required for reconstructing a cross-sectional image, and store a finally reconstructed cross-sectional image. Also, the storage 750 may store a noise-reduced reference image based on image data.

The storage 750 may include at least one storage medium from among a flash memory-type storage medium, a hard disk-type storage medium, a multimedia card micro-type storage medium, card-type memories (e.g., an SD card, an XD memory, and the like), random access memory (RAM), static random access memory (SRAM), read-only memory (ROM), electrically erasable programmable ROM (EE-PROM), programmable ROM (PROM), magnetic memory, a magnetic disc, and an optical disc.

The display 760 displays a predetermined screen. Specifically, the display 760 may display a user interface screen required for performing tomography or a reconstructed cross-sectional image, etc. Also, the display 760 may display at least one of a first reference image, a second reference image, and a target image.

The image processor 720 may control the display 760 to display a predetermined screen. The display 760 allows a user to visually recognize a predetermined image or information by displaying a predetermined screen. The display 760 may correspond to the display illustrated in FIG. 1, and may be a configuration separated from the CT system illustrated in FIG. 1.

The display 760 displays a predetermined screen. Specifically, the display 760 may display a predetermined screen under control of the image processor 720. The display 760 may include a display panel (not shown), and display a user interface screen, a medical image screen, etc. on the display panel.

The display 760 may display a user interface screen receiving a user input in order to perform noise reduction. The display 760 may output various information processed by the tomography apparatus 700 on a screen via a graphical user interface (GUI). Also, the tomography apparatus 700 may include two or more displays 760 depending on an implementation form.

The display 760 may be implemented as at least one of a liquid crystal display, a thin film transistor-liquid crystal display, an organic light-emitting diode, a flexible display, a 3 dimensional (3D) display, and an electrophoretic display.

The user interface 770 generates and outputs a user interface screen for receiving a predetermined command or data from a user, and receives a predetermined command or data from a user via the user interface screen. Also, the user interface screen output from the user interface 770 is output to the display 760. Then, the display 760 may display the user interface screen. A user may view the user interface screen displayed via the display 760, recognize predetermined information, and input a predetermined command or data.

For example, the user interface 770 may include a mouse, a keyboard, or an input unit including hard keys for receiving predetermined data. For example, a user may input predetermined data or command by manipulating at least one of the mouse, the keyboard, or other input units included in the user interface 770.

Also, the user interface 770 may include a touchpad. Specifically, the user interface 770 includes a touchpad (not shown) coupled to a display panel (not shown) included in the display 760, and outputs a user interface screen on the display panel. Also, when a predetermined command is input via the user interface screen, the touchpad may recognize the predetermined command input by a user by detecting the predetermined command.

Specifically, in the case where the user interface 770 includes the touchpad, when a user touches a predetermined point of the user interface screen, the user interface 770 detects the touched point. Also, the user interface 770 may transmit detected information to the image reconstructor 730. Then, the image reconstructor 730 may recognize the user's request or command corresponding to a menu displayed at the detected point, and perform a cross-sectional image reconstruction operation by reflecting the recognized request or command.

The communication module 780 may perform communication with an external device, an external medical apparatus, etc. For example, the communication module 780 may be connected with a CT system or the tomography apparatus 700 externally connected, and may receive the first image data and the second image data. Alternatively, the communication module 780 may receive the first reference image obtained from the first image data and the second reference image obtained from the second image data.

The tomography apparatuses 600 and 700 are applicable to all of a partial angle reconstruction (PAR) method, a full reconstruction method, and a half reconstruction method. Also, the tomography apparatuses 600 and 700 may obtain a cross-sectional image by applying various scan modes. Also, the tomography apparatuses 600 and 700 may apply tomography corresponding to an axial scan method and a helical scan method. Also, the tomography apparatuses 600 and 700 may use an X-ray generator 106 generating a light source having various radiation configurations.

The tomography apparatus 700 may include a central operation processor and generally control operations of the data obtainer 710, the image processor 720, the image reconstructor 730, the gentry 740, the storage 750, the display 760, the user interface 770, and the communication module 780. The central operation processor may include an array of a plurality of logic gates, and include a combination of a general purpose microprocessor and a memory storing a program that may be executed by the microprocessor. Also, a person of ordinary skill in the art will understand that the central operation processor may be implemented by using other forms of hardwares.

Hereinafter, various operations or applications performed by the tomography apparatus 700 are described. Even though one of the data obtainer 710, the image processor 720, the image reconstructor 730, the gentry 740, the storage 750, the display 760, the user interface 770, and the communication module 780 is not specified, content which may be clearly understood or predicted by a person of ordinary skill in the art may be understood by general implementation, and the scope of exemplary embodiments is not limited by a name or a physical/logical structure of a specific component.

FIGS. 8A to 8E are diagrams for explaining a method of performing noise reduction at a tomography apparatus.

Figure 8A:
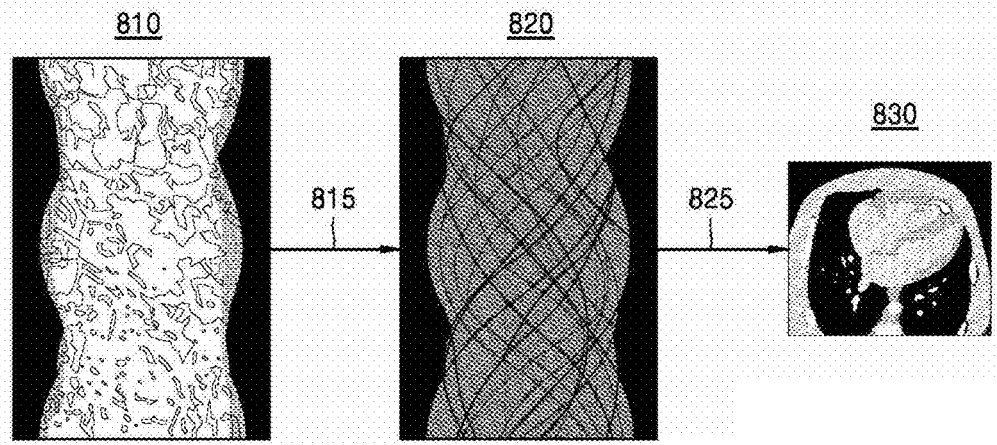
FIGS. 8A to 8E are diagrams for explaining a method of performing noise reduction at a tomography apparatus.

FIG. 8A is a diagram for explaining a process of performing noise reduction of image data obtained via tomography. The tomography apparatus may perform the noise reduction on at least one image data based on a dose of an X-ray detected from at least one of first image data and second image data. The tomography apparatus may perform the noise reduction on the at least one image data by using a low pass filter.

Referring to FIG. 8A, the tomography apparatus obtains image data 810 corresponding to an object. Here, the tomography apparatus may obtain the image data by irradiating an X-ray to the object, or obtain the image data from an external apparatus. The external apparatus is an apparatus for obtaining, storing, processing, or using data related to a CT image, and may be a medical imaging apparatus, a medical server, a portable terminal, or all computing apparatuses that may use and process a medical image. For example, the external apparatus may be a medical diagnosis apparatus included in a medical organization such as a hospital. Also, the external apparatus may be a server for recording and storing a patient's treatment history included in a hospital, a medical imaging apparatus allowing a doctor to read a medical image in a hospital, etc.

The tomography apparatus may reduce noise of image data based on a dose of an X-ray detected from the image data (815). Specifically, the tomography apparatus may analyze a statistical characteristic of data based on a number of electrons of an X-ray detected from image data.

In the case where a number of electrons of the detected X-ray is greater than a predetermined number, the tomography apparatus may determine that noise of image data is small, and generate a reference image corresponding to the image data without removing noise of the image data.

In contrast, in the case where a number of electrons of the detected X-ray is less than a predetermined number, the tomography apparatus may determine noise of image data is large, and remove noise of the image data. The tomography apparatus may perform noise reduction on the image data by using a low pass filter. The low pass filter may be determined from among a plurality of low pass filters based on a number of electrons of the X-ray. The tomography apparatus may obtain noise-free image data 820. Also, the tomography apparatus may obtain the noise-free image data 820 by using a low pass filter for only a portion of the image data. The tomography apparatus may generate a reference image 830 by using noise-free image data (825).

Figure 8B:
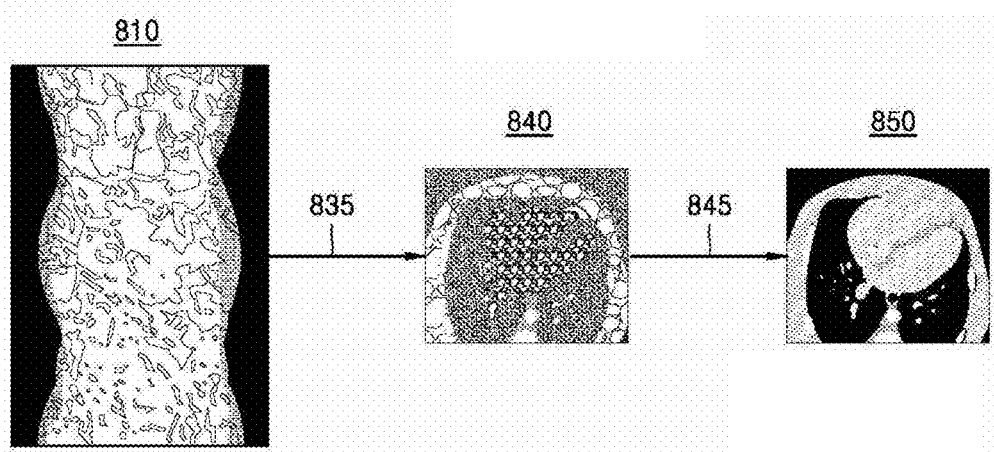

FIG. 8B is a diagram for explaining a process of performing noise reduction of an image obtained from image data. The tomography apparatus may detect an edge region from at least one of a first image obtained from first image data and a second image obtained from second image data, and perform the noise reduction on at least one image based on the edge region. The tomography apparatus may discriminate an edge region from a smooth region in an image, conserve the edge region, and remove noise.

Referring to FIG. 8B, the tomography apparatus obtains an image 840 from image data 810 (835). The tomography apparatus may discriminate noise from an edge on each pixel basis of an image based on a noise model designed for removing noise of the image. The tomography apparatus may change a pixel value of a pixel determined as noise in a direction that reduces noise. The tomography apparatus may generate a reference image 850 by using a noise-free image 840 (845).

Figure 8C:
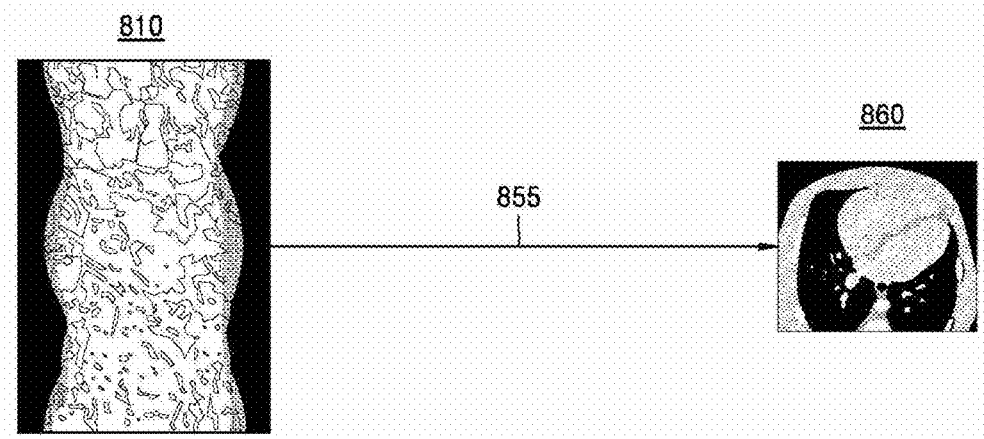

FIG. 8C is a diagram for explaining a process of performing noise reduction by applying a predetermined model to image data. The tomography apparatus may perform the noise reduction by applying a model set in advance to at least one of the first image data and the second imaged data. The model set in advance may be at least one of a model reflecting geometry information of a cross-sectional image to which an X-ray is irradiated (for example, geometry information of the X-ray generator 106, the X-ray detector 108, etc. used for the CT system), a model reflecting a characteristic of an X-ray, and a model reflecting a noise characteristic of a noise model image, and is not limited thereto, which is obvious to a person of ordinary skill in the art. The tomography apparatus may generate a reference image 860 having reduced noise by applying the model set in advance to the image data 810 (855). Also, the tomography apparatus may perform the noise reduction by applying the model set in advance to the image data 810, and perform the noise reduction by repeatedly applying the model set in advance.

Figure 8D:
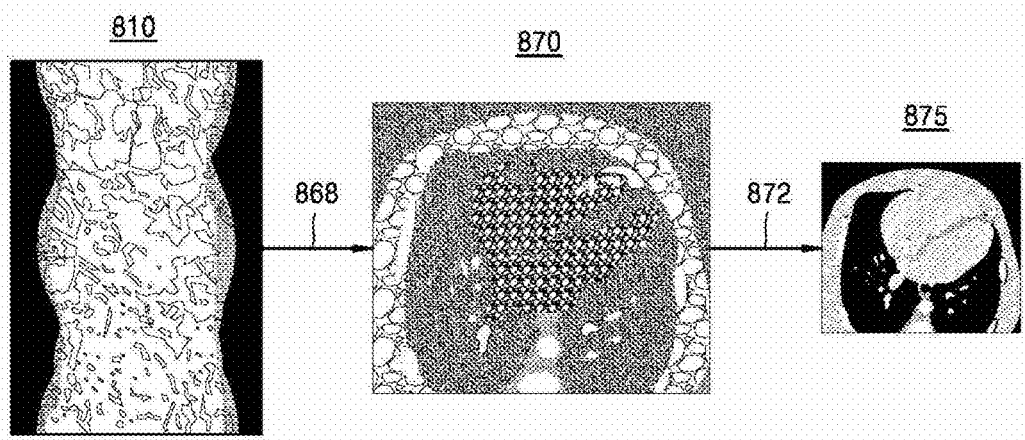

FIG. 8D is a diagram for explaining a process of performing noise reduction by using a size of a voxel inside an image obtained from image data. The tomography apparatus may perform the noise reduction by adjusting a size of a voxel inside a first image obtained from first image data and a size of a voxel inside a second image obtained from second image data. Specifically, the tomography apparatus may reconstruct an image 870 from the image data 810 (868). The tomography apparatus may generate a noise-free image 875 by adjusting a size of a voxel of the reconstructed image 870 (872). For example, in the case where a size of an image is 2 n×2 n, when four voxels are represented by one voxel, a number of all voxels reduces and a size of a voxel increases, so that noise reduces. A method of representing four voxels by using one voxel may represent an average of four voxel values as one voxel value. That is, the tomography apparatus may remove noise by increasing a size of a voxel inside an image.

Figure 8E:
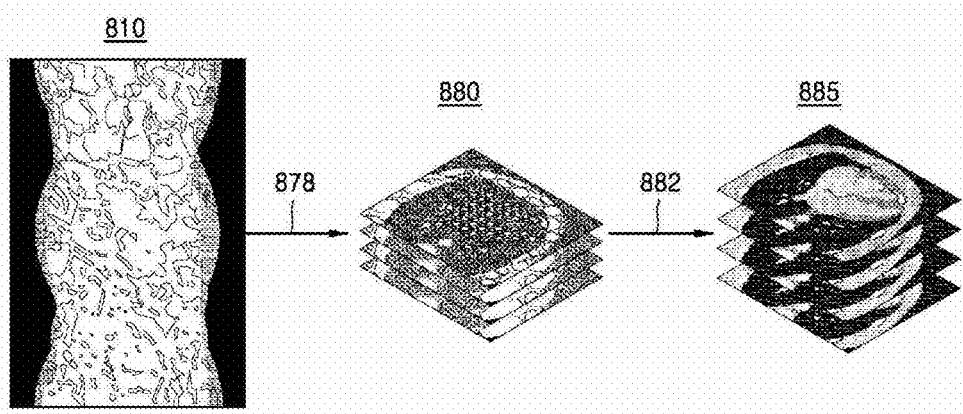

FIG. 8E is a diagram for explaining a process of performing noise reduction by using a thickness of a slice inside an image obtained from image data. The tomography apparatus may perform the noise reduction by adjusting a thickness of a slice inside a first image obtained from first image data, and a thickness of a slice inside a second image obtained from second image data. Specifically, the tomography apparatus may reconstruct an image 880 from image data 810 (878). The tomography apparatus may generate a noise-free image 885 by adjusting a thickness of a slice of the reconstructed image 880 (882). For example, when a thickness of a slice is increased, noise inside an image reduces.

Figure 9A:
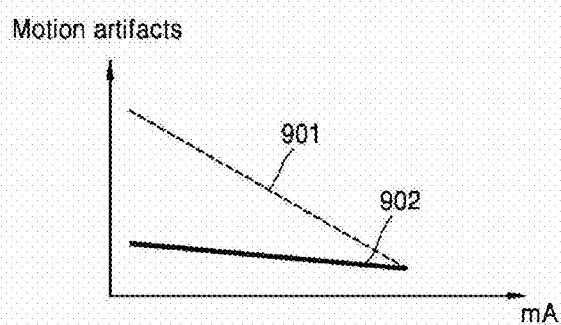
FIGS. 9A to 9C are diagrams for explaining a target image reconstructed based on reference images generated before and after noise reduction is performed.
Figure 9B:
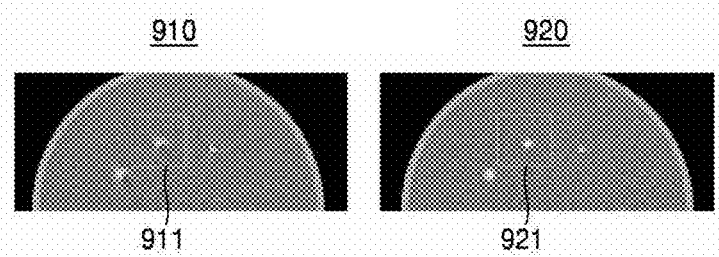
Figure 9C:
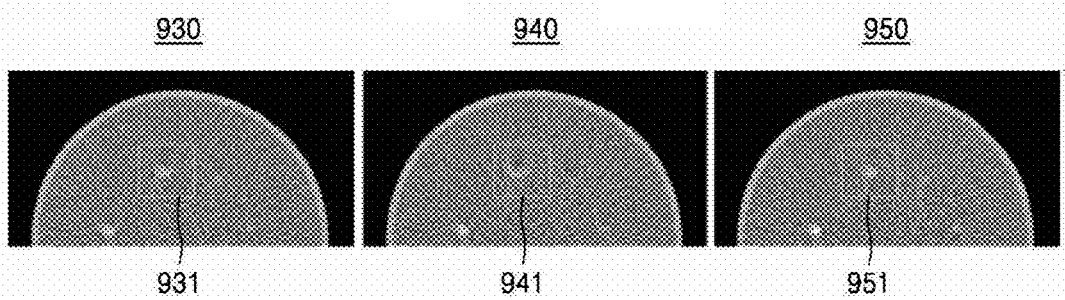

FIGS. 9A to 9C are diagrams for explaining a target image reconstructed based on reference images generated before and after noise reduction is performed.

FIG. 9A is a graph representing motion artifacts depending on a current. In the case where an object serving as an object of CT capturing moves, motion of the object occurs even during one period, and motion artifacts occur due to the motion of the object in reconstructing a CT image.

In the case where the motion artifacts occur, an outermost edge of an object is not clear and overlaps in a reconstructed CT image, and an internal boundary is blurred due to the motion of the object in the CT image.

The motion artifact inside the CT image reduces image quality of a CT image and thus deteriorates accuracy of reading and diagnosis when a user such as a doctor reads an image and diagnoses a disease.

Referring to the graph of FIG. 9A, motion artifacts at a high current is less than motion artifacts at a low current. Also, generally, motion artifacts inside a CT image depending on a current is large under a low current condition. However, in the case where a CT image is reconstructed by using noise-free reference images, a motion artifact under a low current condition is less than a motion artifact of an image reconstructed without using noise-free reference images. That is, a slope 902 of a motion artifact with respect to a current in the case of reconstructing an image by using a noise-free reference image is less than a slope 901 of a motion artifact with respect to a current in the case of reconstructing an image without using a noise-free reference image.

FIG. 9B is a diagram for explaining an image reconstructed under a high current condition. An image 910 of FIG. 9B is an image reconstructed under a high current condition, and an image 920 of FIG. 9B is an image reconstructed by using a noise-free reference image under a high current condition. An inner boundary 911 of the image 910 of FIG. 9B is less clear than an inner boundary 921 of the image 920 of FIG. 9B. The tomography apparatus may reconstruct an image more clearly by using a noise-free reference image.

FIG. 9C is a diagram for explaining an image reconstructed under a low current condition. An image 930 of FIG. 9C is an image reconstructed under a low current condition, an image 940 of FIG. 9C is an image reconstructed by using motion information of an object inside an image under a low current condition, and an image 950 of FIG. 9C is an image reconstructed by using motion information of an object inside a noise-free reference image under a low current condition. As illustrated in FIG. 9C, the tomography apparatus may minimize motion artifacts when reconstructing a target image by using a noise-free reference image. That is, an inner boundary 951 of the image 950 is clearer than an inner boundary 931 of the image 930 and an inner boundary 941 of the image 940.

Figure 10:
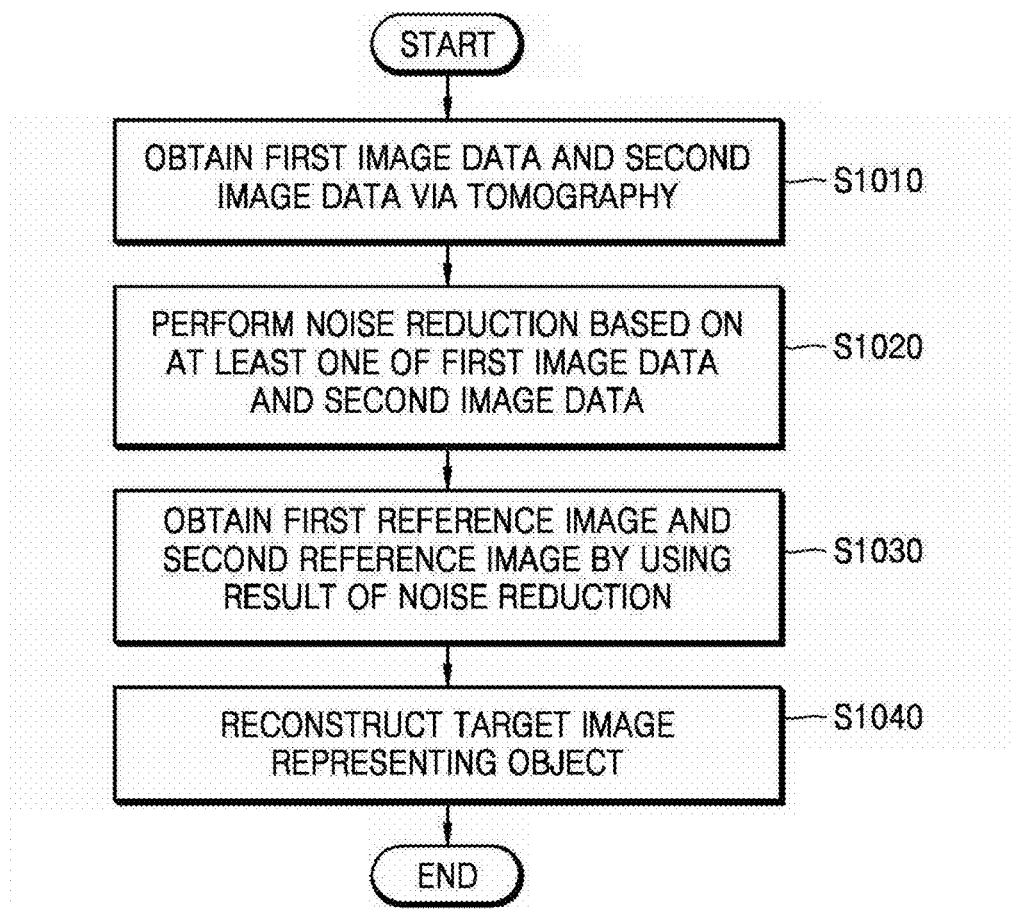
FIG. 10 is a flowchart illustrating a method of reconstructing a cross-sectional image according to an exemplary embodiment.

FIG. 10 is a flowchart illustrating a method of reconstructing a cross-sectional image according to an exemplary embodiment.

Referring to operation S1010 of FIG. 10, a tomography apparatus may obtain first image data and second image data via tomography. Here, the first image data is data obtained by irradiating an X-ray to an object at a first point, and the second image data is data obtained by irradiating an X-ray to the object at a second point. The tomography apparatus may obtain image data by directly irradiating an X-ray to the object, and may obtain image data from an external apparatus.

The first image data and the second image data may be obtained from at least one of an X-ray based on a first threshold dose, an X-ray based on a first threshold voltage, and an X-ray based on a first threshold current.

Figure 11:
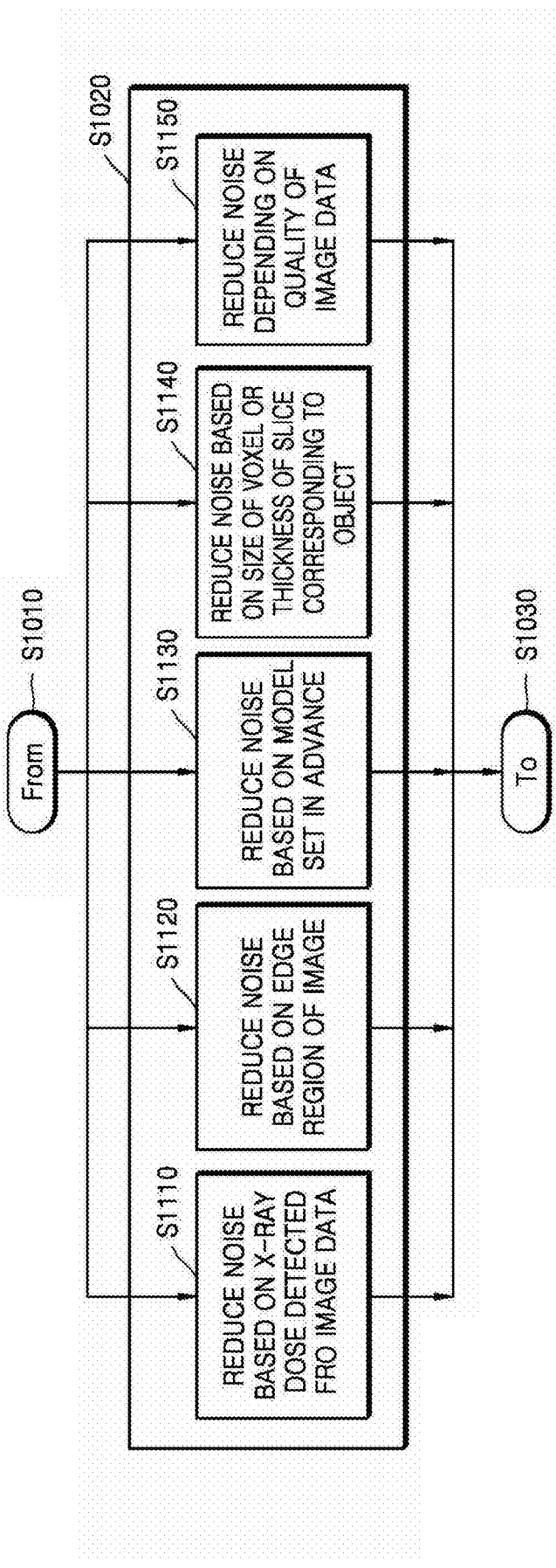
FIG. 11 is a flowchart illustrating a method of reconstructing a cross-sectional image according to another exemplary embodiment.

Referring to operation S1020, the tomography apparatus may perform noise reduction based on at least one of the first image data and the second image data. FIG. 11 is a diagram for explaining operation S1020 of FIG. 10. Operations S1110, S1120, S1130, S1140, and S1150 of FIG. 11 may be performed in parallel.

Referring to operation S1110, the tomography apparatus may reduce noise based on an X-ray dose detected from image data. The tomography apparatus may perform noise reduction on the first image data and the second image data from among a plurality of image data. Specifically, the tomography apparatus may remove noise inside image data by using a low pass filter.

Referring to operation S1120, the tomography apparatus may reduce noise based on an edge region of an image. The tomography apparatus may detect an edge region from at least one of a first image obtained from the first image data and a second image obtained from the second image data, and perform noise reduction on at least one image while conserving the edge region.

Referring to operation S1130, the tomography apparatus may perform noise reduction by applying a model set in advance to at least one of the first image data and the second image data. Here, the model set in advance may include at least one of a model reflecting geometry information of the tomography apparatus irradiating the X-ray, a model reflecting a characteristic of the X-ray, and a model reflecting a noise characteristic, and is not limited thereto.

Referring to operation S1140, the tomography apparatus may perform the noise reduction by adjusting a size of a voxel inside the first image obtained from the first image data and a size of a voxel inside the second image obtained from the second image data. For example, when a size of a voxel is increased, noise may reduce.

Referring to operation S1150, the tomography apparatus may perform noise reduction by adjusting a thickness of a slice obtained from the first image data, and a thickness of a slice obtained from the second image data. For example, when a thickness of a slice is increased, noise may reduce.

Referring to operation S1020, the tomography apparatus may determine quality of the first image data and the second image data, and determine whether to perform the noise reduction depending on the determined quality. The quality may be determined based on at least one of a dose of the X-ray and a condition under which the X-ray is irradiated. That is, when noise is greater than a predetermined criterion, the tomography apparatus may remove noise of image data.

In operation S1030, the tomography apparatus may obtain a first reference image corresponding to the first image data and a second reference image corresponding to the second image data by using a result of the noise reduction.

In operation S1040, the tomography apparatus may reconstruct a target image representing an object. Specifically, the tomography apparatus may obtain motion information estimating motion of an object based on the first reference image and the second reference image. The tomography apparatus may reconstruct the target image representing the object at a target point based on the motion information.

The above-described apparatus may be implemented by using a hardware component, a software component, and/or a combination of a hardware component and a software component. For example, the apparatus and the component described in the exemplary embodiments may be implemented by using one or more general purpose computers or special purpose computers like a processor, a controller, an arithmetic logic unit (ALU), a digital signal processor, a microcomputer, a field programmable array (FPA), a programmable logic unit (PLU), a microprocessor, or any apparatus that may execute an instruction and respond thereto.

A processor may perform an operating system (OS) and one or more software applications performed on the OS. Also, the processor may access, store, manipulate, process, and generate data in response to execution of software.

For convenience of understanding, though a case where one processor is used has been described, a person of ordinary skill in the art will understand that the processor may include a plurality of processing elements and/or processing elements of a plurality of types. For example, the processor may include a plurality of processors, or one processor and one controller. Also, a different processing configuration like a parallel processor may be used.

Software may include a computer program, a code, an instruction, or a combination of one or more of these, or configure a processor so that the processor may operate as desired, or instruct the processor independently or collectively.

Software and/or data may be embodied permanently or temporarily in a certain type of a machine, component, physical apparatus, virtual equipment, a non-transitory computer-readable recording medium or apparatus, or a transmitted signal wave in order to be read by a processor or to provide a command or data to the processor. Software may be distributed on a computer system connected via a network, and stored or executed in a distributed fashion. Software and data may be stored in one or more non-transitory computer-readable recording media.

The methods according to exemplary embodiments may be embodied in the form of program commands executable through various computer means, which may be recorded on a non-transitory computer-readable recording medium. The non-transitory computer-readable recording medium may include program commands, data files, and data structures either alone or in combination. The program commands recorded on the non-transitory computer-readable recording medium may be those that are especially designed and configured for the exemplary embodiments, or may be those that are known and available to computer programmers skilled in the art.

Examples of the non-transitory computer-readable recording medium include magnetic recording media such as hard disks, floppy disks, and magnetic tapes, optical recording media such as CD-ROMs and DVDs, magneto-optical recording media such as floptical disks, and hardware devices such as ROMs, RAMs, and flash memories that are especially configured to store and execute program commands.

Examples of the program commands include machine language codes that may be generated by a compiler, and high-level language codes that may be executed by a computer by using an interpreter.

In order to perform operations of the exemplary embodiments, the hardware apparatus may be configured to operate as one or more software modules, and vice versa.

Though the exemplary embodiments have been described with reference to limited exemplary embodiments and drawings, a person of ordinary skill in the art will understand that various modifications and changes may be made therein from the descriptions. For example, even when the described technologies are performed in a sequence different from the described method, and/or components such as the described system, structure, apparatus, and circuit are coupled or combined in a form different from the described method, or replaced or substituted by other components or equivalents, a proper result may be accomplished.

Therefore, the scope should not be determined by the described exemplary embodiments, and should be determined by not only the following claims but also equivalents thereof.

What is claimed is:

1. A tomography apparatus comprising:
at least one processor configured to:
obtain first image data at a first point and second image data at a second point using tomography, the tomography being performed by irradiating an X-ray to an object;
perform noise reduction based on at least one from among the first image data and the second image data, and to obtain a first reference image corresponding to the first image data and a second reference image corresponding to the second image data using a result of the performed noise reduction; and
reconstruct a target image representing the object based on the first reference image and the second reference image,
wherein the at least one processor is further configured to perform the noise reduction by adjusting a size of a voxel inside a first image obtained from the first image data and a size of a voxel inside a second image obtained from the second image data.

2. The apparatus of claim 1, wherein the at least one processor is further configured to obtain motion information estimating a motion of the object based on the first reference image and the second reference image, and to reconstruct the target image representing the object at a target point based on the motion information.

3. The apparatus of claim 1, wherein the first image data and the second image data are obtained from at least one from among an X-ray based on a first threshold dose, an X-ray based on a first threshold voltage, and an X-ray based on a first threshold current.

4. The apparatus of claim 1, wherein the at least one processor is further configured to perform the noise reduction based on a dose of the X-ray detected from the at least one from among the first image data and the second image data.

5. The apparatus of claim 4, wherein the at least one processor is further configured to perform the noise reduction using a low pass filter.

6. The apparatus of claim 1, wherein the at least one processor is further configured to detect an edge region from at least one of a first image obtained from the first image data and a second image obtained from the second image data, and to perform the noise reduction based on the edge region.

7. The apparatus of claim 6, wherein the at least one processor is further configured to remove noise while conserving the edge region.

8. The apparatus of claim 1, wherein the at least one processor is further configured to perform the noise reduction by applying a predetermined model to at least one of the first image data and the second image data.

9. The apparatus of claim 8, wherein the predetermined model comprises at least one from among a model reflecting geometry information of a tomography apparatus irradiating the X-ray, a model reflecting a characteristic of the X-ray, and a model reflecting a noise characteristic.

10. The apparatus of claim 1, wherein the at least one processor is further configured to perform the noise reduction by adjusting a thickness of a slice obtained from the first image data and a thickness of a slice obtained from the second image data.

11. The apparatus of claim 1, wherein the at least one processor is further configured to determine a quality of the first image data and the second image data, and to determine whether to perform the noise reduction depending on the determined quality.

12. The apparatus of claim 11, wherein the quality is determined based on at least one from among a dose of the X-ray and a condition under which the X-ray is irradiated.

13. The apparatus of claim 1, further comprising:
a display configured to display at least one from among the first reference image, the second reference image, and the target image.

14. The apparatus of claim 1, further comprising:
a user interface configured to receive a user input using a user interface screen to perform the noise reduction; and
a display configured to display the user interface screen.

15. The apparatus of claim 1, further comprising:
a user interface configured to receive a user input for selecting the first image data and the second image data from among image data corresponding to a plurality of points based on the tomography.

16. The apparatus of claim 1, wherein the first reference image differs from the second reference image in at least one from among a size of the object, a location of the object, and a shape of the object.

17. The apparatus of claim 1, wherein the adjusting of the size of the voxel inside the first image comprises increasing the size of the voxel inside the first image.

18. The apparatus of claim 1, wherein the adjusting of the size of the voxel inside the first image comprises reducing a number of voxels in the first image.

19. A method of reconstructing a cross-sectional image, the method comprising:
obtaining first image data at a first point and second image data at a second point using tomography, the tomography being performed by irradiating an X-ray to an object;
performing noise reduction based on at least one from among the first image data and the second image data;
obtaining a first reference image corresponding to the first image data and a second reference image corresponding to the second image data using a result of the performed noise reduction; and
reconstructing a target image representing the object based on the first reference image and the second reference image,
wherein the performing of the noise reduction comprises adjusting a size of a voxel inside a first image obtained from the first image data and a size of a voxel inside a second image obtained from the second image data.

20. The method of claim 19, wherein the reconstructing of the target image representing the object comprises:
obtaining motion information estimating a motion of the object based on the first reference image and the second reference image; and
reconstructing the target image representing the object at a target point based on the motion information.

21. A non-transitory computer-readable recording medium having recorded thereon a program for executing a method of reconstructing a cross-sectional image, the method comprising:
obtaining first image data at a first point and second image data at a second point using tomography, the tomography being performed by irradiating an X-ray to an object;
performing noise reduction based on at least one from among the first image data and the second image data;
obtaining a first reference image corresponding to the first image data and a second reference image corresponding to the second image data using a result of the performed noise reduction; and
reconstructing a target image representing the object based on the first reference image and the second reference image,
wherein the performing of the noise reduction comprises adjusting a size of a voxel inside a first image obtained from the first image data and a size of a voxel inside a second image obtained from the second image data.

* * * * *